US008960897B2

(12) United States Patent
Nadolny et al.

(10) Patent No.: US 8,960,897 B2
(45) Date of Patent: Feb. 24, 2015

(54) DEVICE FOR DEMONSTRATING AND TESTING THE EFFICACY OF AN ANTIREFLECTION TREATMENT OF AN OPHTHALMIC LENS

(75) Inventors: Carole Nadolny, Charenton-le-Pont (FR); Fabien Calandrini, Charenton-le-Pont (FR); Catherine Fauquier, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 156 days.

(21) Appl. No.: 13/643,129

(22) PCT Filed: Apr. 14, 2011

(86) PCT No.: PCT/FR2011/050868
§ 371 (c)(1),
(2), (4) Date: Oct. 24, 2012

(87) PCT Pub. No.: WO2011/138536
PCT Pub. Date: Nov. 10, 2011

(65) Prior Publication Data

US 2013/0038832 A1 Feb. 14, 2013

(30) Foreign Application Priority Data

May 5, 2010 (FR) ..................................... 10 53517

(51) Int. Cl.
*G02C 7/02* (2006.01)
*G01M 11/02* (2006.01)
*G01N 21/84* (2006.01)

(52) U.S. Cl.
CPC ....... *G01M 11/0264* (2013.01); *G01N 21/8422* (2013.01)
USPC ..................................................... 351/159.01

(58) Field of Classification Search
CPC .... G02B 1/043; G02B 1/041; G03F 7/70591; G03F 7/7085; G01N 21/958; G01N 2021/9511; G01N 21/55; G01N 2021/9583; G01N 2021/9586; G01J 1/0407; G01J 1/0455; C09D 5/006
USPC ................... 356/124, 239.2, 445; 351/159.01
See application file for complete search history.

(56) References Cited

U.S. PATENT DOCUMENTS

| | | | | |
|---|---|---|---|---|
| 2,566,058 A | | 8/1951 | Elizabeth Donohue | |
| 3,729,839 A | * | 5/1973 | Bourdier | 434/371 |

(Continued)

FOREIGN PATENT DOCUMENTS

| | | | | |
|---|---|---|---|---|
| DE | 10 2007 028364 | | 12/2008 | |
| FR | 2941056 | * | 7/2010 | G02B 1/11 |
| WO | 2008023134 | | 2/2008 | |

OTHER PUBLICATIONS

Patentscope English translation of French Publication N. 2941056.*

(Continued)

*Primary Examiner* — Tarifur Chowdhury
*Assistant Examiner* — Mohamed Amara
(74) *Attorney, Agent, or Firm* — Sofer & Haroun, LLP

(57) ABSTRACT

A device is provided for demonstrating and testing the effectiveness of an anti-reflection treatment of an ophthalmic lens. An image (2) is backlit by a light source (7) with a second face (1B) forming an angle of at least 90° relative to the first face and is placed facing a third face (1C) for positioning at least one ophthalmic lens (4A) with its concave face facing outwards. The device includes text (5) on a transparent medium behind the mirror and a face of uniform color (6) behind the text, such that when a user looks through the orifice (4) and the lens (4A), the user can see the reflection of the image (2) on the lens (4A) by means of the mirror (3), the image being superposed on the text (5) and on the face (6) of uniform color.

13 Claims, 1 Drawing Sheet

(56) References Cited

U.S. PATENT DOCUMENTS

| | | | | |
|---|---|---|---|---|
| 5,272,364 | A * | 12/1993 | Hironaka | 257/185 |
| 6,113,238 | A | 9/2000 | Balch et al. | |
| 7,621,750 | B1 * | 11/2009 | Boinard et al. | 434/365 |
| 2007/0081256 | A1 * | 4/2007 | Travers | 359/630 |
| 2008/0124699 | A1 | 5/2008 | Reiber | |
| 2011/0069304 | A1 | 3/2011 | Carole et al. | |

OTHER PUBLICATIONS

International Search Report dated Dec. 20, 2010.

* cited by examiner

DEVICE FOR DEMONSTRATING AND TESTING THE EFFICACY OF AN ANTIREFLECTION TREATMENT OF AN OPHTHALMIC LENS

RELATED APPLICATIONS

This application is a National Phase Application of PCT/FR2011/050868, filed on Apr. 14, 2011, which in turn claims the benefit of priority from French Patent Application No. 10 53517 filed on May 5, 2010, the entirety of which are incorporated herein by reference.

BACKGROUND

1. Field of the Invention

The invention relates to demonstrating and testing in comparative manner the effectiveness of anti-reflection treatment of an ophthalmic lens.

2. Description of Related Art

There exists devices for measuring optical properties of an anti-reflection treatment by means of a system of the complex spectrometer type for measuring reflection. These optical properties are mean reflection $R_m$, visual reflection $R_v$, chrome C, and hue angle h.

There also exists a method of demonstrating the effectiveness of anti-reflection treatment in which the performance of a lens having anti-reflection treatment is compared with a lens not having such treatment, by means of right and left images that are reflected on right and left ophthalmic lenses worn by a wearer of an eyeglass frame in which one of the lenses has been subjected to anti-reflection treatment while the other has not been subjected to such treatment. The reflections of the images are viewed by the wearer when looking into a central mirror, or else by an observer. The wearer or the observer compares the difference in the anti-reflection effectiveness of the two lenses.

That type of method is not associated with any protocol and is therefore relatively inaccurate and random insofar as it depends on observation conditions.

Patent document US 2008/0124699 describes a demonstrator device having a part with a first face for supporting an image and a second face for supporting a mirror, which mirror is semi-reflective.

That device is for showing the effect of polarizing lenses or of lenses that are said to reduce polarized glare. Light is polarized naturally when a light ray is reflected with an angle of incidence equal to the Brewster angle on a surface that is plane, e.g. the ground or a sheet of water, and it becomes polarized linearly. Such lenses, by virtue of being polarized on a perpendicular axis, eliminate that reflected light or glare as perceived by the wearer of the lens.

According to that document, in the absence of polarizing lenses, the wearer sees firstly a first image that is not polarized and placed behind the mirror constituted by a semi-reflective film, and secondly a second image that is horizontally polarized after being reflected on the semi-reflective film. When the wearer views the demonstrator while using lenses that are polarized perpendicularly to the polarization axis of the second image, the polarizing filter effect of the lens enables the second image to be eliminated and the wearer sees only the first image.

That device, which is specifically adapted to testing polarizing lenses, cannot be used for testing the effectiveness of anti-reflection treatment that consists in attenuating reflections on the face of the lens visible from the outside by external people, and not by the wearer.

OBJECTS AND SUMMARY

The object of the present invention is quite different, being to provide a device for demonstrating and testing the effectiveness of anti-reflection treatment of an ophthalmic lens, which device while likewise comprising a part having a first face for supporting an image and a second face for supporting a semi-reflective mirror, is specifically designed for this purpose.

The device is simple to use and can be used equally well as a demonstrator for opticians and as equipment constituting instrumentation, and it is easy to use by untrained people. The device makes it possible to evaluate differences of less than 0.5% in visual reflection $R_v$ between two anti-reflection treatments.

To do this, the invention provides a device for demonstrating and testing the effectiveness of anti-reflection treatment of an ophthalmic lens, the device comprising a part having a first face for supporting an image and a second face for supporting a mirror, which mirror is a semi-reflective mirror, the device being characterized in that said image is backlit by a light source, said second face forms an angle of at least 90° relative so said first face and is placed facing a third face for positioning at least one ophthalmic lens with its concave face facing outwards, the third face being provided with an arrangement for positioning said lens and including at least one orifice arranged in said third face, the device also including text on a transparent medium behind said mirror and a face of uniform color behind said text, such that when a user looks through said orifice and said lens, the user can see the reflection of said image on said lens by means of said mirror, which image is superposed on said text and on said face of uniform color.

Because the second face supporting the semi-reflective mirror forms an angle of at least 90° relative to the first face carrying the image, and because of the positioning arrangement of the lens, the image is reflected directly on the lens and it is this reflection of greater or lesser extent depending on the effectiveness of the anti-reflection treatment of the lens that is subsequently reflected by the mirror and that becomes superposed on the text carried by the first face.

Furthermore, in order to obtain a device that is effective, the image is backlit by a light source so as to increase the brightness of the reflection of said image on the lens and thereby properly test the anti-reflection treatment.

Finally, by using a text behind the semi-reflective mirror, the test device is particularly effective and easy to use, causing the tester to perform a reading action and giving a test result that may clearly be determined depending on the possibility, the difficulty, or the impossibility of reading the text.

The invention also provides the use of such a device, which use is characterized in that it consists: in positioning a lens on said orifice, the lens being provided on a first half with a first anti-reflection treatment and being provided on a second half with a second anti-reflection treatment, the lens being positioned with its concave face facing outwards; in looking through the lens; and in determining the trouble caused by viewing the reflection resulting on said mirror while reading said text in order to compare the reflection levels of the reflections of said image as reflected on said first half and on said second half.

BRIEF DESCRIPTION OF THE DRAWINGS

The invention is described below in detail with the help of figures that merely show preferred embodiments of the invention.

DETAILED DESCRIPTION

Figure 1:
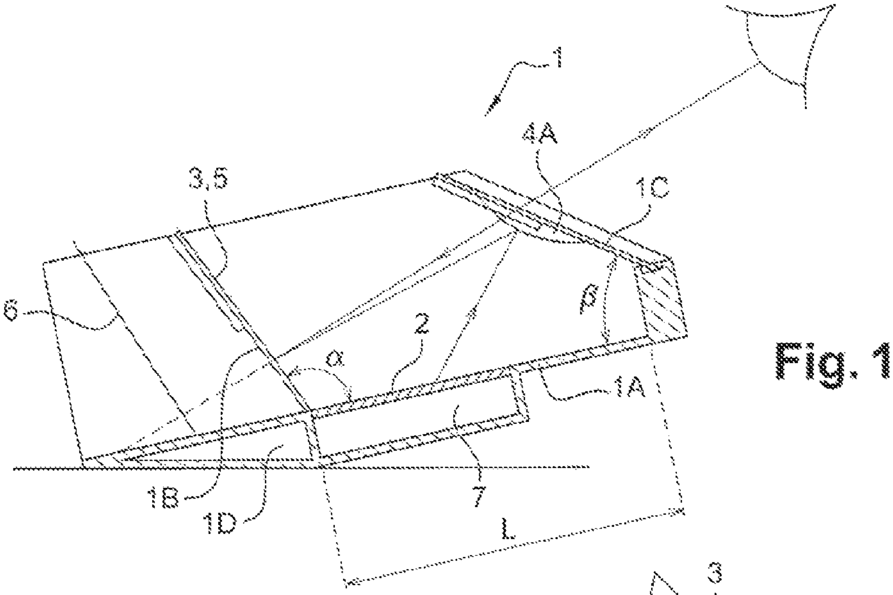
FIG. 1 is a vertical section view of a device in accordance with the invention for demonstrating and testing the effectiveness of anti-reflection treatment for an ophthalmic lens.
Figure 2:
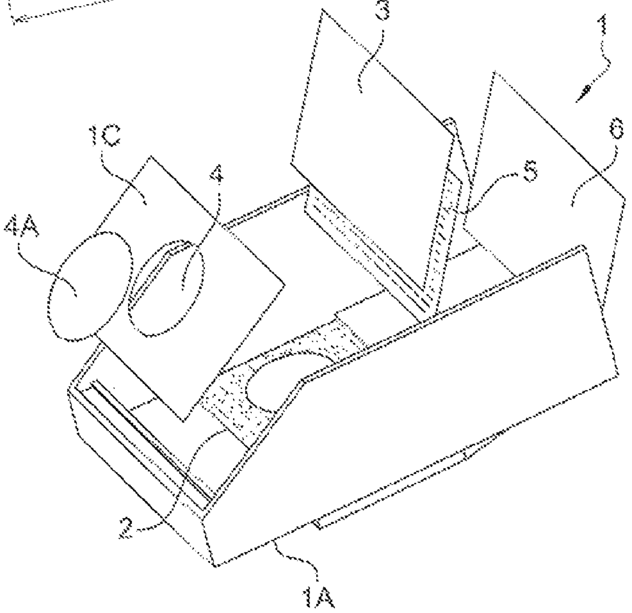
FIG. 2 is an exploded perspective view of the device.

FIGS. 1 and 2 show a device 1 for demonstrating and testing the quality of anti-reflection treatment on an ophthalmic lens.

The device 1 comprises a part made of transparent plastics material constituted by a channel-section member having a web constituting a medium with a first face 1A for supporting an image 2 stuck to said face and backlit by a light source 7, and flanges supporting a second face 1B for supporting a semi-reflective mirror 3, preferably a two-way mirror presenting visual reflection $R_v$ of about 55%, and forming an angle of at least 90° relative to the first face 1A, and a third face 1C for positioning at least one ophthalmic lens 4A, situated facing the second face 1B and provided with an arrangement including at least one orifice for positioning the lens on said third face 1C, and for example an installation angle bracket arranged under the orifice 4 in the third face. The ophthalmic lens is arranged with its concave face turned towards the outside.

The orifice 4 is circular and has a diameter of about 50 millimeters (mm).

The third face 1C is frosted, in order to avoid any interfering reflections on the mirror 3.

The device 1 also includes text 5, preferably black in color, supported on a transparent medium placed behind the semi-reflective mirror 3, and a face of uniform color, preferably of white color 6 to maximize contrast with the text and located behind the mirror so that when a user looks through the orifice 4 and the lens 4A, the user can see the reflection resulting from the image 2 on the lens by means of said mirror, superposed on the text and on the face of white color.

The face 6 of white color may be placed against the mirror 3 or it may be spaced apart therefrom, as shown in FIG. 1.

The semi-reflective mirror 3, which is preferably in the form of a film, enables the text 5 to be observed in transmission while also allowing the reflection of the image 2 on the lens 4A to be observed in reflection.

The second face 113 is preferably inclined at an angle α of about 110° relative to the first face 1A. The third face is preferably inclined at an angle β lying in the range 40° C. to 60° relative to the first face. The length L of the first face 1A between the second face 1B and the third face 1C lies in the range 15 centimeters (cm) to 30 cm, and is preferably about 17 cm.

The part 1 also preferably includes a counterweight 1D serving to tilt it as shown in FIG. 1 so as to ensure that it is comfortably positioned relative to an observer when placed on a horizontal surface. Adjustable legs may be installed at the front of the part 1 so as to enable the tilt angle of the device to be adjusted relative to the supporting table, thereby improving reading comfort or adapting to the size of the user. Comfortable observation may correspond to an angle of about 15° relative to the horizontal plane.

Figure 3:
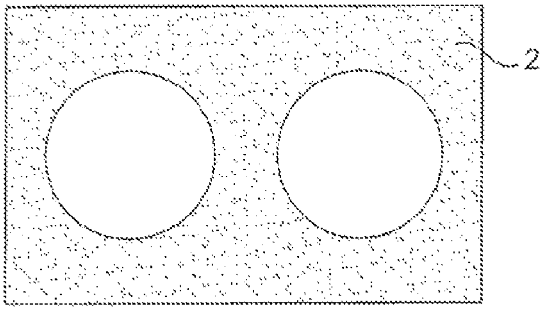
FIG. 3 is a detail view.

The image 2 shown in FIG. 3 presents a matt black background with two matt white patterns at contrast of 100%. The pattern is preferably of a neutral and non-illustrative shape, such as two disks, for example. The two disks are symmetrical about the central plane of symmetry of the device. The neutral shape is to enable the observer to concentrate on reading the text without being influenced by the shape of the reflection.

These patterns are made on a translucent medium and a source of light 7 is placed under the first face, under the pattern. By way of example, two neon mini-lamps having a power of 3 watts (W) may be used. The effect of the lamps is to increase the brightness of the reflection of the image 2 on the lens. The brightness of the lamps may be adjustable.

By virtue of the dimensions selected for the part 1 and for the image 2, and by virtue of the brightness selected for the lamps, the reflection of the image 2 is of size and brightness sufficient to enable the observer to perceive the reflection of the image 2 reflected on the lens, which lens is provided on a first half with a first anti-reflection treatment and is provided on a second half with a second anti-reflection treatment, the anti-reflection treatment of lesser effectiveness presenting a reflection of the image that is more visible. The perceived reflection thus presents a size of the order of 1 cm to 3 cm.

Using a lens that has been treated with two different anti-reflection treatments on respective halves makes it easier to evaluate the difference in the brightness of the reflection of the image on each of the anti-reflection treatments.

The device is used by taking a lens that is provided with a first anti-reflection treatment on a first half with a second anti-reflection treatment on a second half and placing it on said orifice with its concave side facing outwards. The separation between the two halves is positioned vertically relative to the device. The observer uses both eyes to observe through the lens and determine the trouble caused by viewing the resulting reflection on said mirror while reading said text, to compare the reflection levels of the reflections of said image reflected on said first half and on said second half.

Use is performed in a well-lit environment, preferably lit with daylight, presenting light intensity of about 205 lux.

The embodiments described have a plane image 2.

This image is preferably centered on the vertical plane containing the direction of the observer's gaze, and in the embodiment shown, it is centered on the plane of symmetry containing the center of the lens-positioning orifice, assuming that the observer is situated immediately in front of the lens.

The mirror 3 is a plane mirror, preferably of square or round symmetrical shape. It is centered on the lens-positioning orifice.

The lens may be placed on the third face 1C as described above, or it may for example be adhesively bonded to said face.

In order to avoid disturbing viewing through the lens, the lens is preferably a planar spherical a focal lens.

The invention claimed is:

1. A device for demonstrating and testing the effectiveness of anti-reflection treatment of an ophthalmic lens, the device comprising:

- a part having a first face for supporting a physical target having an image thereon and a second face for supporting a mirror, which mirror is a semi-reflective mirror,
- wherein said image on said target is backlit by a light source, said second face forms an angle of at least 90° relative to said first face and is placed facing a third face for positioning at least one ophthalmic lens with its concave face facing outwards, the third face being provided with an arrangement for positioning said lens and including at least one orifice arranged in said third face, the device also including text on a transparent medium behind said mirror and a face of uniform color behind said text, such that when a user looks through said orifice and said lens, the user can see the reflection of said image from said target on said lens by means of said mirror, which image is superposed on said text and on said face of uniform color.

2. A device according to claim 1, wherein said text is black in color and said face is white in color.

3. A device according to claim 1, wherein said part is a channel-section member, having its flanges supporting said second face and said third face.

4. A device according to claim 1, wherein said third face is inclined at an angle lying in the range 40° to 60° relative to the first face.

5. A device according to claim 1, wherein said second face is inclined at an angle of about 110° relative to the first face.

6. A device according to claim 1, wherein the length of the first face between said second face and said third face lies in the range 15 cm to 30 cm.

7. A device according to claim 1, wherein said image on said target is an image presenting a matt black background and at least one matt white pattern.

8. A device according to claim 7, wherein said pattern is made on a translucent medium.

9. A device according to claim 7, wherein said pattern comprises two disks.

10. A device according to claim 1, wherein the brightness of the light source is adjustable.

11. A device according to claim 1, wherein said third face is frosted.

12. A method to employ the device according to claim 1, said method comprising the steps of:

positioning a lens on an orifice, the lens being provided on a first half with a first anti-reflection treatment and being provided on a second half with a second anti-reflection treatment, the lens being positioned with its concave face facing outwards;

looking through the lens; and determining a difference in the brightness of the reflection of the image on each of the anti-reflection treatments by viewing the reflection resulting on said mirror while reading said text in order to compare the reflection levels of the reflections of said image as reflected on said first half and on said second half.

13. The method of claim 12, wherein said step of determining a difference in the brightness of the reflection of the image on each of the anti-reflection treatments is performed with both eyes.

* * * * *